(12) United States Patent
DeFelice et al.

(10) Patent No.: US 10,881,529 B2
(45) Date of Patent: Jan. 5, 2021

(54) SPINAL IMPLANT AND METHOD FOR FABRICATING THE SAME

(71) Applicants: Scott DeFelice, Holyoke, MA (US); Anthony DeCarmine, Lebanon, CT (US)

(72) Inventors: Scott DeFelice, Holyoke, MA (US); Anthony DeCarmine, Lebanon, CT (US)

(73) Assignee: Oxford Performance Materials, Inc., South Windsor, CT (US)

(*) Notice: Subject to any disclaimer, the term of this patent is extended or adjusted under 35 U.S.C. 154(b) by 45 days.

(21) Appl. No.: 16/136,968

(22) Filed: Sep. 20, 2018

(65) Prior Publication Data

US 2019/0015217 A1    Jan. 17, 2019

Related U.S. Application Data

(63) Continuation of application No. 14/828,099, filed on Aug. 17, 2015, now Pat. No. 10,105,240.
(Continued)

(51) Int. Cl.
*A61F 2/30*    (2006.01)
*B29C 64/153*  (2017.01)
(Continued)

(52) U.S. Cl.
CPC .......... *A61F 2/447* (2013.01); *A61F 2/30771* (2013.01); *A61F 2/44* (2013.01); *B29C 64/153* (2017.08); *B33Y 10/00* (2014.12); *B33Y 80/00* (2014.12); *A61F 2/3094* (2013.01); *A61F 2002/3097* (2013.01); *A61F 2002/30205* (2013.01); *A61F 2002/30322* (2013.01); *A61F 2002/30593* (2013.01);
(Continued)

(58) Field of Classification Search
CPC ...................................................... A61F 2/447
See application file for complete search history.

(56) References Cited

U.S. PATENT DOCUMENTS 9,173,748 B2 * 11/2015 Cook .................... A61F 2/4425
9,301,853 B2 *  4/2016 Richter ................. A61F 2/4425
(Continued)

FOREIGN PATENT DOCUMENTS

WO    2011126490 A1   10/2011
WO    2013085947 A1    6/2013
WO    2014018325 A1    1/2014

OTHER PUBLICATIONS

U.S. Office Action U.S. Appl. No. 14/828,099 dated Nov. 7, 2017 12 pages.
(Continued)

*Primary Examiner* — Tessa M Matthews
(74) *Attorney, Agent, or Firm* — Welsh IP Law LLC (57) ABSTRACT

A spinal implant is provided that includes a body extending in direction at least substantially along a body axis, between a first end portion and a second end portion. The spinal implant also includes a first bearing surface disposed relative to the first end portion, and defining a first relief pattern that is configured to inhibit movement of the spinal implant relative to one or more vertebrae in at least substantially all directions. A method for manufacturing the spinal implant involves use of selective laser sintering.

16 Claims, 12 Drawing Sheets

Related U.S. Application Data (60) Provisional application No. 62/039,148, filed on Aug. 19, 2014.

(51) Int. Cl.
*B33Y 10/00* (2015.01)
*B33Y 80/00* (2015.01)
*A61F 2/44* (2006.01)
*B29K 71/00* (2006.01)
*B29L 31/00* (2006.01)

(52) U.S. Cl.
CPC ............ *A61F 2002/30841* (2013.01); *A61F 2002/30878* (2013.01); *A61F 2002/30894* (2013.01); *A61F 2002/30968* (2013.01); *B29K 2071/00* (2013.01); *B29L 2031/7532* (2013.01)

(56) References Cited

U.S. PATENT DOCUMENTS

| | | |
|---|---|---|
| 2005/0251260 A1 | 11/2005 | Gerber et al. |
| 2007/0100454 A1 | 5/2007 | Burgess et al. |
| 2007/0100456 A1* | 5/2007 | Dooris ............... A61F 2/4611 623/17.14 |
| 2007/0270956 A1* | 11/2007 | Heinz ................. A61F 2/44 623/17.11 |
| 2009/0276051 A1* | 11/2009 | Arramon ............. C08L 71/00 623/17.16 |
| 2010/0217395 A1 | 8/2010 | Bertagnoli et al. |
| 2011/0035010 A1* | 2/2011 | Harrington ......... A61F 2/4425 623/17.16 |
| 2011/0046668 A1* | 2/2011 | Goraltchouk .... A61B 17/06166 606/228 |
| 2012/0316650 A1 | 12/2012 | Ullrich, Jr. et al. |
| 2015/0018958 A1 | 1/2015 | Ullrich, Jr. et al. |
| 2015/0173915 A1 | 6/2015 | Laubert et al. |

OTHER PUBLICATIONS

U.S. Office Action U.S. Appl. No. 14/828,099 dated Jul. 19, 2017 pp. 15.

\* cited by examiner

SPINAL IMPLANT AND METHOD FOR FABRICATING THE SAME

CROSS-REFERENCE TO RELATED APPLICATION

The present disclosure is a continuation application of pending U.S. patent application Ser. No. 14/828,099 filed Aug. 17, 2015, which claims the benefit under 35 U.S.C. § 119 (e) to U.S. Provisional Patent Application No. 62/039,148, filed Aug. 19, 2014. All prior applications are herein incorporated by reference in their entirety.

FIELD OF THE INVENTION

The present invention relates to a medical interbody implant, and more specifically relates to a spinal implant that defines a bearing surface configured to inhibit movement of the implant relative to one or more adjacent vertebra and to promote fusion of the adjacent vertebra to the spinal implant. The present invention further relates to a method of manufacturing a spinal implant, and more specifically a method of using selective laser sintering to manufacture a spinal implant having the bearing surface.

BACKGROUND OF THE INVENTION

Figure 1:
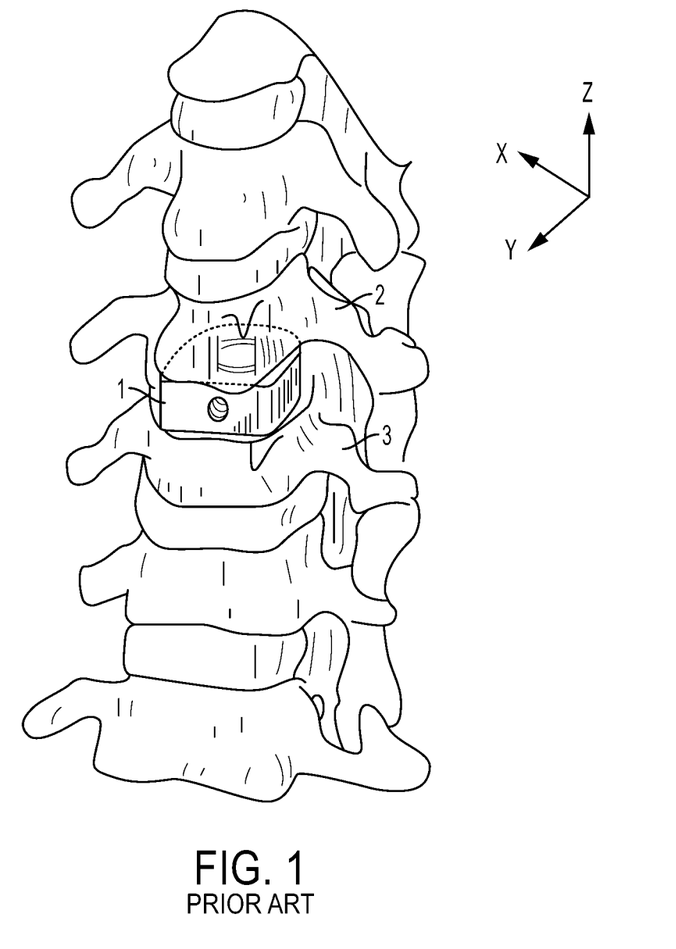
FIG. 1 illustrates a perspective view of a human spine with a prior art spinal implant.

Spinal fusion is a surgical technique in which a spinal implant is used to join one or more vertebrae. In preparation for the spinal fusion, the one or more intervertebral discs between the vertebrae are removed. The spinal implant is surgically inserted between the vertebrae in order to maintain spine alignment and intervertebral disc height. FIG. 1, for example, illustrates a prior art spinal implant 1 inserted between adjacent first and second vertebrae 2, 3. The spinal implant can be made from various different materials, including, for example, a plastic and/or a metal (e.g., titanium). After the spinal implant is surgically inserted between the vertebrae, the vertebrae fuse with bearing surfaces defined on opposing ends of the spinal implant. The fusion process typically takes between 6 to 12 months after surgery. The post-surgery fusion process can be augmented by the placement of screws, rods, plates, and/or cages related to one or more of the vertebrae in order to stabilize the vertebrae and facilitate bone fusion.

A disadvantage of known spinal implants is that external forces can cause a movement (also known as "slippage" or "floating") of the spinal implant relative to one or more of the vertebrae. The likelihood of such a translation is particularly high during the period between 6 to 12 months after surgery, when the fusion process typically takes place. Such movement is disadvantageous, because the positioning of the spinal implant relative to the vertebrae requires a high degree of precision in order to provide the desired therapeutic effect. Any unwanted movement can negatively impact any therapeutic and any benefit to the patient.

Figure 2:
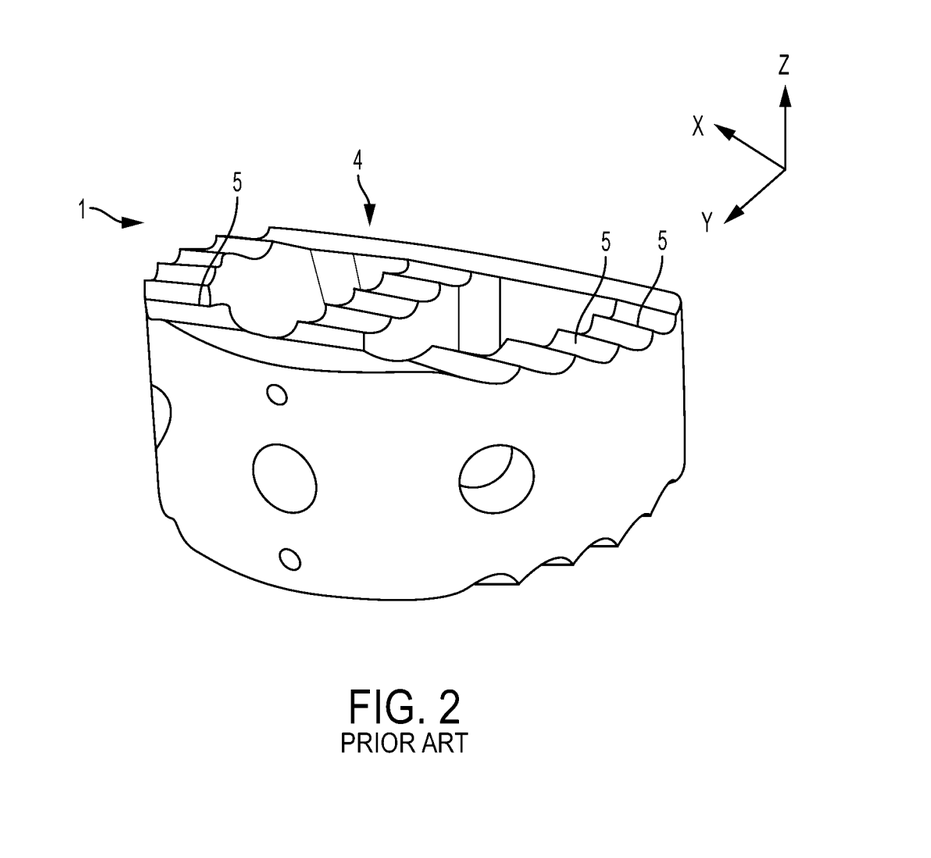
FIG. 2 illustrates a perspective view of another prior art spinal implant.
Figure 3:
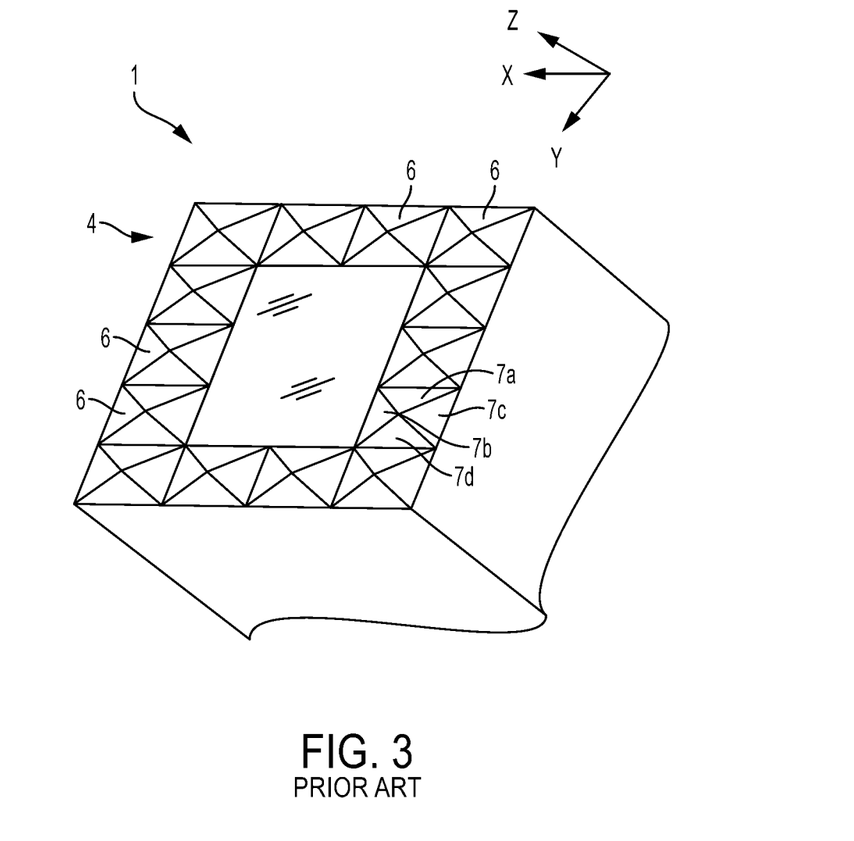
FIG. 3 illustrates a perspective view of another prior art spinal implant.

It is known to form a relief pattern on one or more bearing surfaces of the spinal implant in an attempt to inhibit movement of the spinal implant relative to a vertebra in a direction extending parallel and/or perpendicular to a bearing surface of the vertebra. FIG. 2, for example, illustrates a prior art spinal implant 1 having a top bearing surface 4 that defines a plurality of linear grooves and ridges 5 in the top bearing surface 4 of the prior art spinal implant 1. The grooves and ridges 5 aid in inhibiting movement of the spinal implant 1 relative to a vertebra (not shown) in a widthwise direction extending perpendicular to the grooves and ridges 5. However, the grooves and ridges 5 do not inhibit movement of the spinal implant 1 relative to a vertebra (not shown) in a lengthwise direction extending parallel to the grooves and ridges 5 or in other directions parallel to a plane defined by the top bearing surface 4. FIG. 3 illustrates another prior art spinal implant 1 having a top bearing surface 4 that defines a plurality of pyramids 6 extending therefrom. The pyramids 6 aid in inhibiting movement of the spinal implant 1 relative to a vertebra (not shown) in a lengthwise-extending direction in which opposing first and second faces 7a, 7b of the pyramid 6 are directed, and a widthwise-extending direction in which opposing third and fourth faces 7c, 7d of the pyramid 6 are directed. However, the pyramids 6 do not inhibit movement of the spinal implant 1 relative to the vertebra in other directions parallel to a plane defined by the bearing surface 4, or in a heightwise-extending vertical direction relative to the plane.

Aspects of the present invention are directed to these and other problems.

SUMMARY OF THE INVENTION

According to an aspect of the present invention, a spinal implant is provided that includes a body extending in direction at least substantially along a body axis, between a first end portion and a second end portion. The spinal implant also includes a first bearing surface disposed relative to the first end portion, and defining a first relief pattern that is configured to inhibit movement of the spinal implant relative to one or more vertebrae in at least substantially all directions.

According to another aspect of the present invention, a method for manufacturing a spinal implant is provided that includes the step of selective laser sintering a body extending in direction at least substantially along a body axis, between a first end portion and a second end portion, and having a first bearing surface disposed relative to the first end portion, the first bearing surface defining a first relief pattern that is configured to inhibit movement of the spinal implant relative to one or more vertebrae in at least substantially all directions.

In addition to, or as an alternative to, one or more of the features described above, further aspects of the present invention can include one or more of the following features, individually or in combination:

the spinal implant further includes second bearing surface disposed relative to the second end portion, and defining a second relief pattern that is configured to inhibit movement of the spinal implant relative to one or more vertebrae in at least substantially all directions;

the first bearing surface defines a plurality of protrusions integrally connected therewith, and extending therefrom, which collectively define the first relief pattern;

the plurality of protrusions each have an at least generally conical shape, and each defining a base integrally connected to the first bearing surface, and a tip at a distal end of the respective protrusion;

the base defines a base width, the tip defines a tip width, and the base width is greater than the tip width;

at least one of the plurality of protrusions is configured such that the tip overhangs the base;

at least one of the plurality of protrusions has a hook-like conical shape;

the tip is truncated, blunted, and/or rounded;

the base defines a tapered and/or convex surface that provides a smooth and/or rounded transition between the surface of the respective protrusion and the first bearing surface;

each of the plurality of protrusions extends along a protrusion axis that passes through an apex of the respective protrusion;

at least one of the plurality of protrusions is oriented obliquely relative to the first bearing surface;

the plurality of protrusions define a plurality of angles between the respective protrusions and the first bearing surface;

the respective angles are randomly selected to be within a predetermined range of angles;

the plurality of protrusions are oriented in a plurality of different directions relative to the body axis;

the respective orientations are randomly selected;

each of the plurality of protrusions extends along a protrusion axis that passes through an apex of the respective protrusion; and the respective protrusion axes extend in generally all directions towards and/or away from the body axis;

the body defines a plurality of side surfaces extending substantially perpendicular to the first bearing surface between the first end portion and the second portion of the body; and the respective protrusion axes of the plurality of protrusions intersect with respective planes defined by each of the plurality of side surfaces at a plurality of positions on the respective planes;

the plurality of protrusions define a plurality of heights extending between their respective tips and the first bearing surface;

the respective heights are randomly selected;

the respective heights of the plurality of protrusions is between 1 mm and 3 mm;

the selective laser sintering step involves using a laser to selectively fuse a polymeric powder material;

the polymeric powdered material is a polyaryletherketone ("PAEK") powder material; and the PAEK powder material includes at least one material selected from the group consisting of: polyetheretherketone ("PEEK"), polyetherketone ketone ("PEKK"), polyetherketone ("PEK"), polyetheretherketoneketone ("PEEKK") or polyetherketoneetherketoneketone ("PEKEKK").

These and other aspects of the present invention will become apparent in light of the drawings and detailed description provided below.

DETAILED DESCRIPTION OF THE INVENTION

Referring to FIGS. 4-15, the present disclosure describes a spinal implant 10, and a method for manufacturing the spinal implant 10.

The present disclosure describes aspects of the present invention with reference to the exemplary embodiments illustrated in the drawings; however, aspects of the present invention are not limited to the exemplary embodiments illustrated in the drawings. The present disclosure may describe one or more features as having a length extending relative to an x-axis, a width extending relative to a y-axis, and/or a height extending relative to a z-axis. The drawings illustrate the respective axes.

Figure 4:
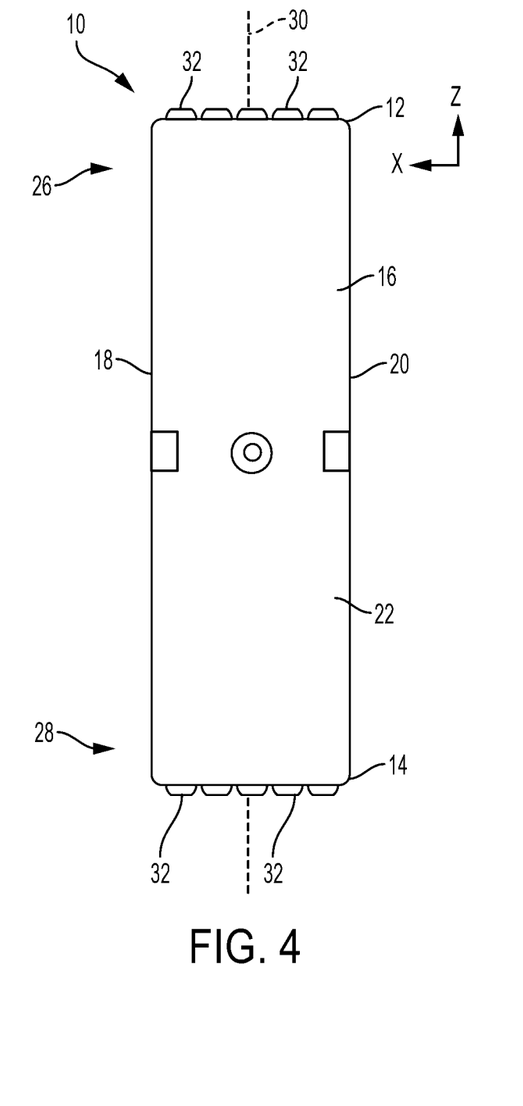
FIG. 4 illustrates a front elevation view of a first embodiment of the present spinal implant.
Figure 5:
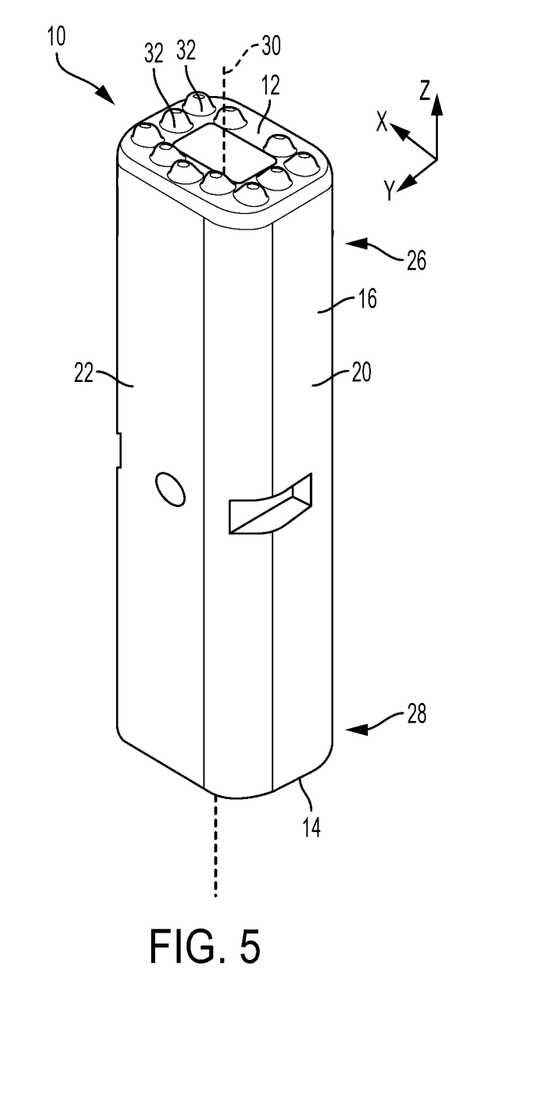
FIG. 5 illustrates a perspective view of the spinal implant of FIG. 4.
Figure 6:
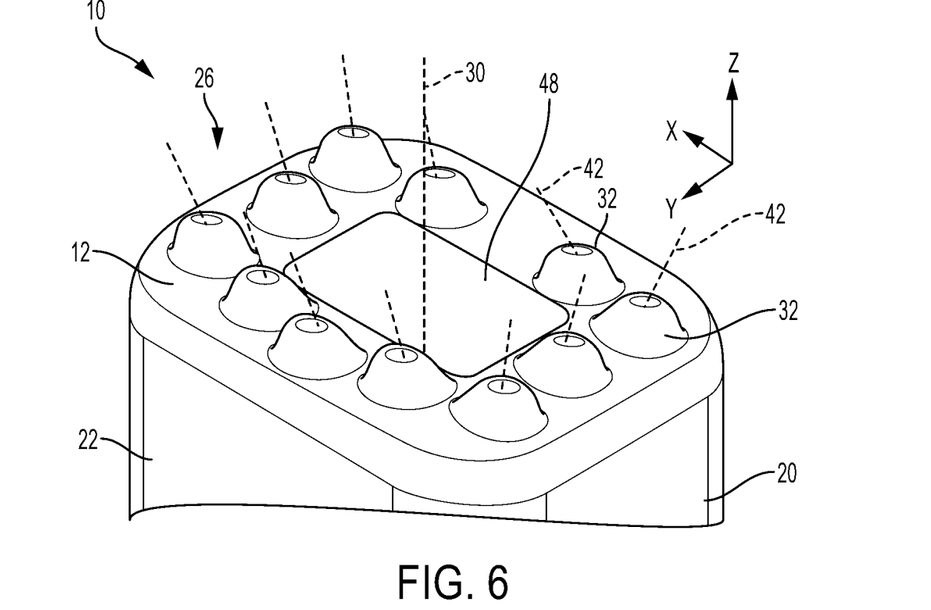
FIG. 6 illustrates a perspective view of the top end portion of the spinal implant of FIG. 4.
Figure 7:
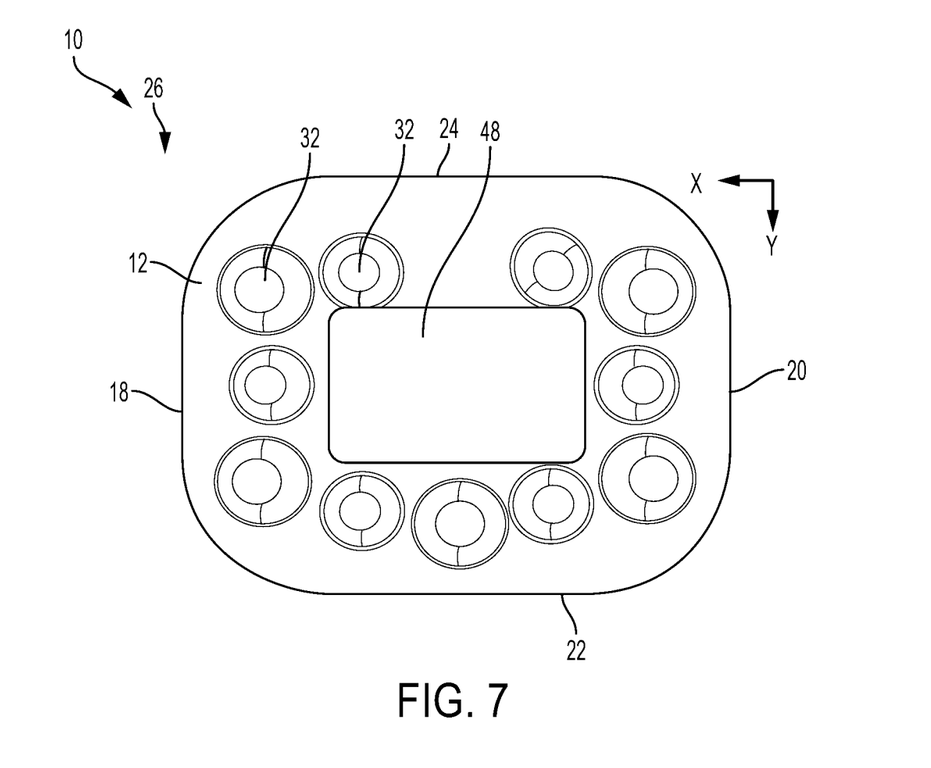
FIG. 7 illustrates a plan view of the top end portion of the spinal implant of FIG. 4.

Referring to FIGS. 4 and 5, the spinal implant 10 includes a first bearing surface 12 and a second bearing surface 14 positioned at opposing ends of the spinal implant 10. The first and second bearing surfaces 12, 14 each define a relief pattern that is configured to inhibit movement of the spinal implant 10 relative to one or more vertebrae in at least substantially all directions. The present spinal implant 10 thus offers significant advantages over prior art spinal implants, which only prevent such movement in some directions.

The spinal implant 10 includes a body 16 that: (ii) extends in a lengthwise direction between a first side surface 18 and a second side surface 20; (iii) extends in a widthwise direction between a front surface 22 and a rear surface 24; and (iii) extends in a heightwise direction between a first end portion 26 and an opposing second end portion 28 at least substantially along a body axis 30. The first bearing surface 12 is disposed relative to the first end portion 26, and the second bearing surface 14 is disposed relative to the second end portion 28. The distance between the first and second end portions 28, 30 is equal to or less than approximately 3 inches.

The first and second bearing surfaces 12, 14 each define a plurality of protrusions 32 integrally connected therewith, and extending therefrom, which collectively define the respective relief patterns of the first and second bearing surfaces 12, 14.

Figure 8:
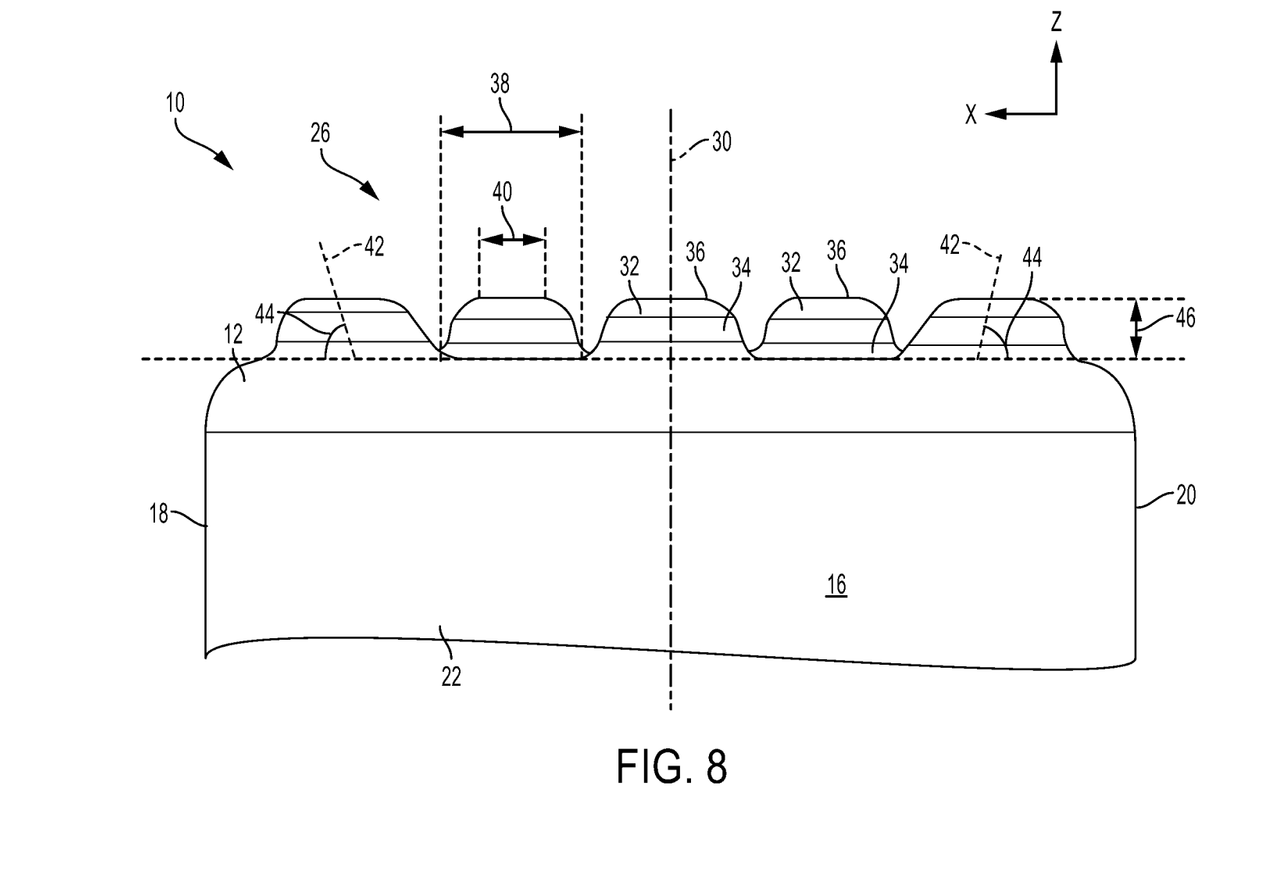
FIG. 8 illustrates a front elevation view of the top end portion of the spinal implant of FIG. 4.
Figure 9:
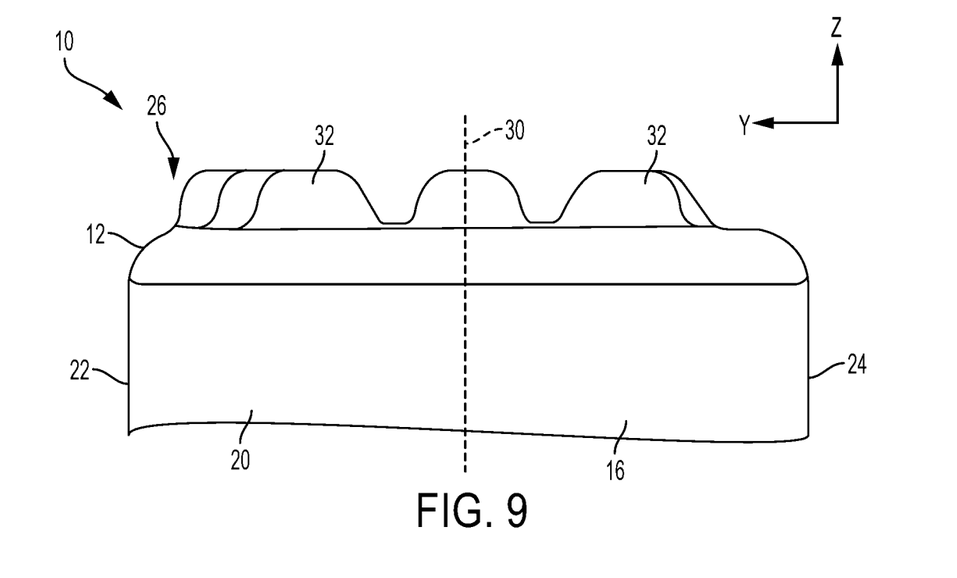
FIG. 9 illustrates a side elevation view of the top end portion of the spinal implant of FIG. 4.
Figure 10:
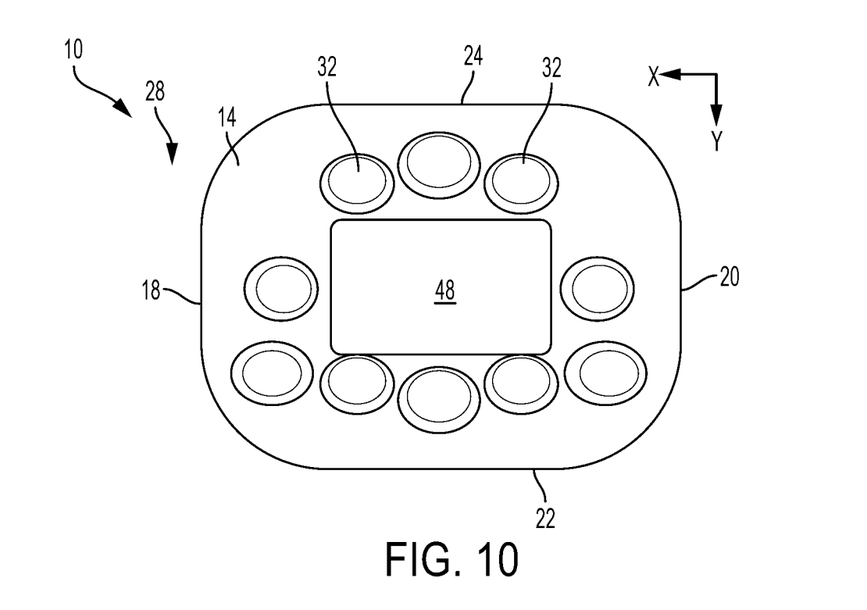
FIG. 10 illustrates a plan view of the bottom end portion of the spinal implant of FIG. 4.
Figure 12:
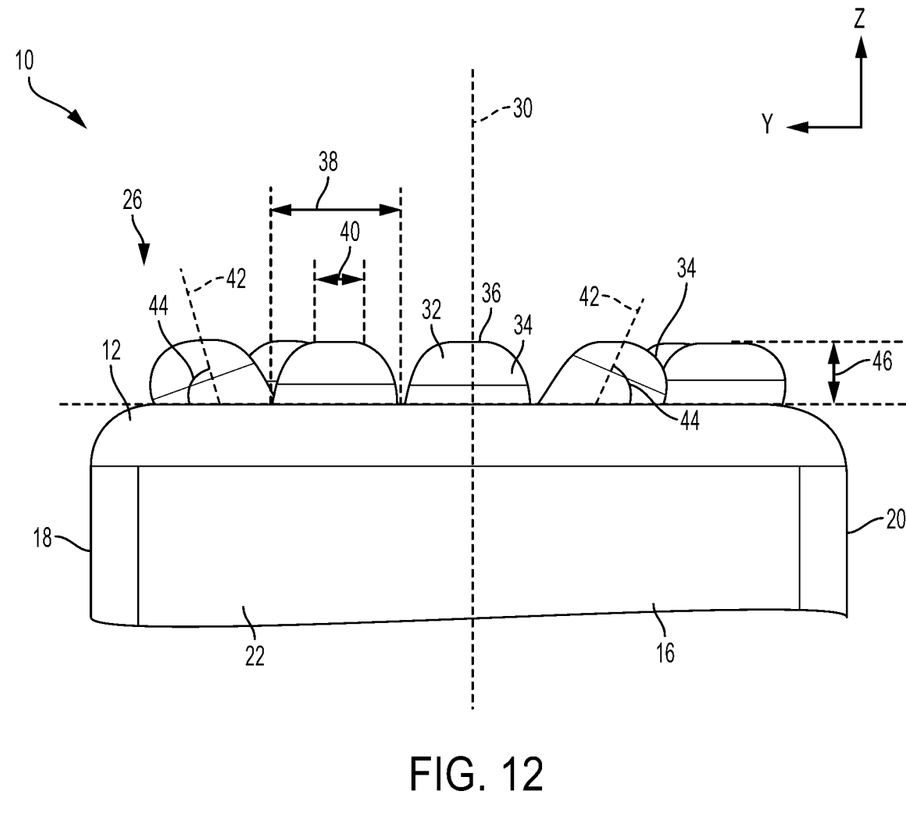
FIG. 12 illustrates a side elevation view of the top end portion of the spinal implant of FIG. 11.
Figure 13:
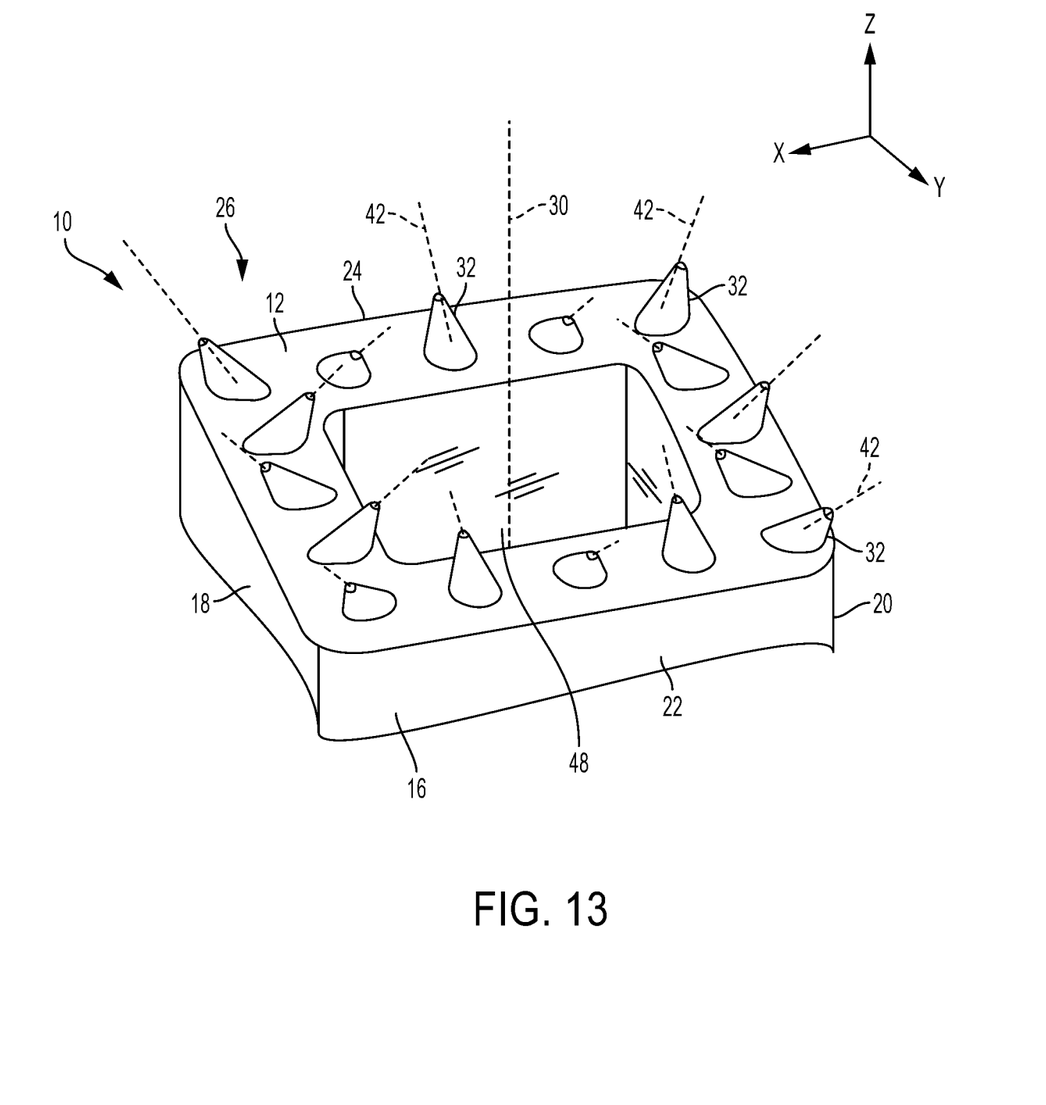
FIG. 13 illustrates a perspective view of the top end portion of a third embodiment of the present spinal implant.
Figure 14:
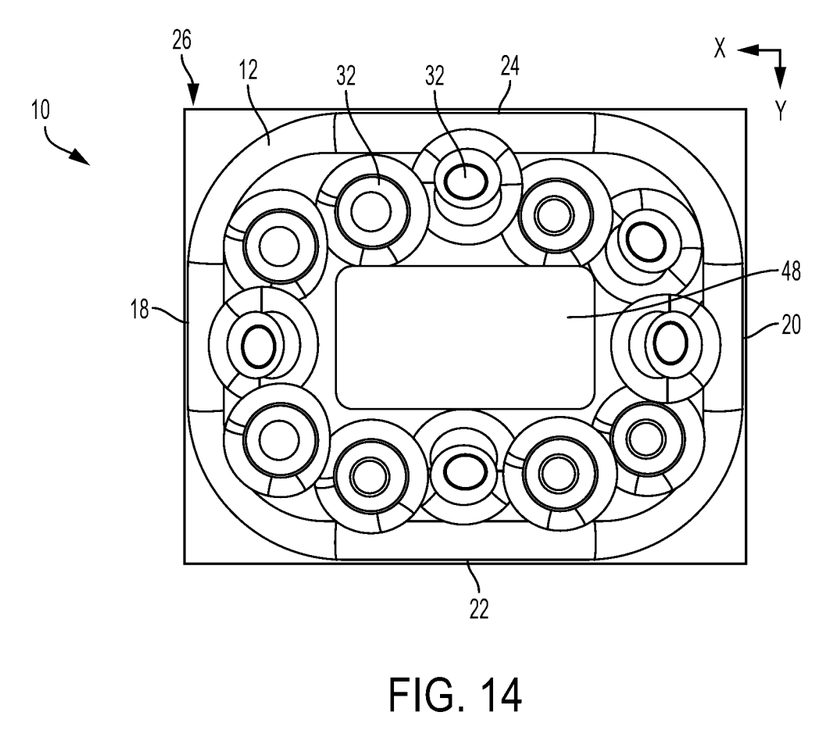
FIG. 14 illustrates a plan view of the top end portion of a fourth embodiment of the present spinal implant.

Referring to FIGS. 8 and 12, the protrusions 32 each have an at least generally conical shape. The protrusions 32 each define a base 34 integrally connected to the respective bearing surface 12, 14, and a tip 36 at a distal end of the protrusion 32. The base 34 defines a base width 38, and the tip 36 defines a tip width 40. The base width 38 is greater than the tip width 40.

In some embodiments (see FIGS. 4-12 and 14-15), the tip 36 of each protrusion 32 is truncated, blunted, and/or rounded. In some embodiments (see FIGS. 6, 8, 9, etc.), the base 34 of each protrusion 32 defines a tapered or convex surface that provides a smooth and/or rounded transition between the surface of the protrusion 32 and the respective bearing surface 12, 14 with which it is integrally formed.

In some embodiments (see, e.g., FIG. 13), at least one of the protrusions 32 is configured such that the tip 36 of the protrusion 32 overhangs the base 34 of the protrusion 32. That is, the tip 36 of the protrusion 32 passes through a plane extending perpendicular to the respective bearing surface 12, 14 at the perimeter of the protrusion base 34. In some of these and other embodiments, the protrusions 32 can have a tooth-like or hook-like conical shape. In such embodiments, the protrusions 32 can effectively form a "hook" that can engage a vertebra in an interlocking event, which can thereby inhibit relative movement of the spinal implant 10 relative to the vertebra along an axis at least substantially perpendicular to the respective bearing surface 12, 14 of the spinal implant 10.

Figure 11:
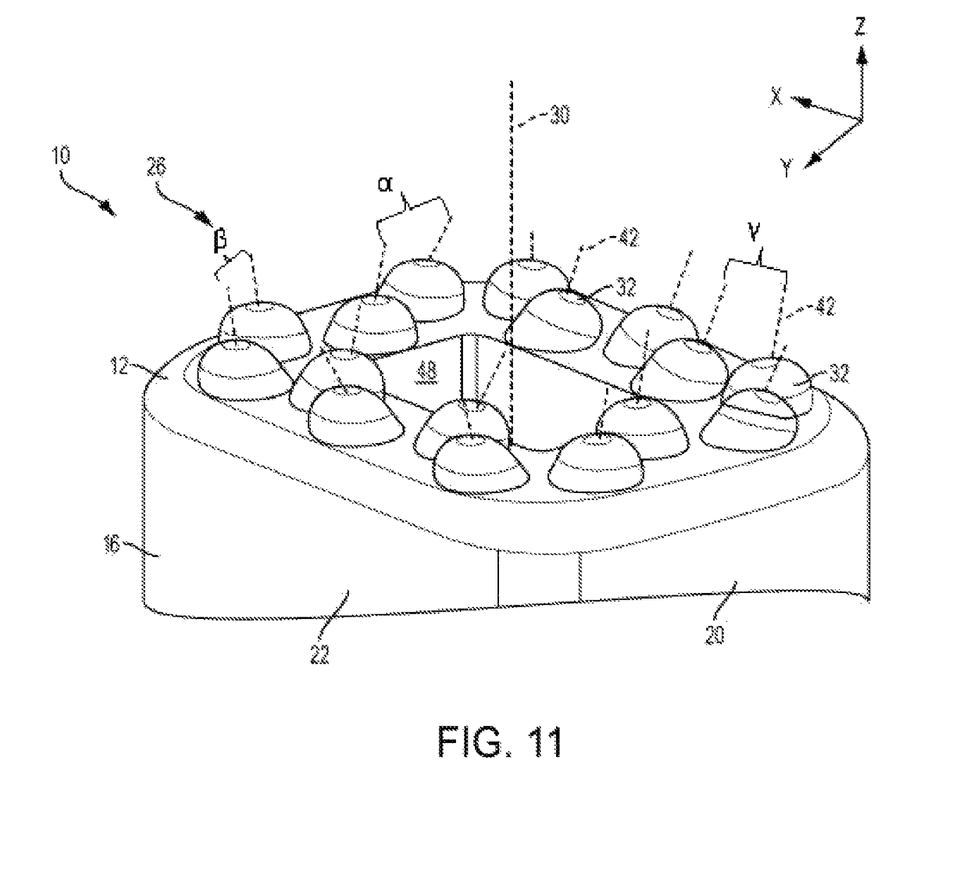
FIG. 11 illustrates a perspective view of the top end portion of a second embodiment of the present spinal implant.

Referring to FIGS. 6, 8, and 11-13, the protrusions 32 each extend along a protrusion axis 42 that passes through the apex of the protrusion 32. One or more of the protrusions 32 are oriented obliquely relative to the respective bearing surface 12, 14 with which they are integrally formed. That is, the respective protrusion axes 42 are disposed at one or more non-parallel and non-perpendicular angles 44 relative to the body axis 30. Referring to FIG. 11, an angle β is formed between a first pair of protrusions, an angle α is formed between a second pair of protrusions, and an angle γ is formed between a third pair of protrusions.

Referring to FIGS. 8 and 12, in some embodiments, the protrusions 32 on a respective bearing surface 12, 14 can define a plurality of different angles 44 between the respective protrusion axes 42 and the respective bearing surface 12, 14. In such embodiments, the angles 44 of the protrusions 32 can be randomly selected (e.g., by a drafting program or the like), or can have the appearance of being randomly selected, within a predetermined range (e.g., between 10° and 80°).

Referring to FIGS. 6, 11, 13, and 14, in some embodiments, the protrusions 32 on a respective bearing surface 12, 14 can be oriented in a plurality of different directions relative to the body axis 30. In some embodiments, the respective protrusion axes 42 collectively extend in generally all directions towards and/or away from the body axis 30. In some embodiments, the respective protrusion axes 42 intersect with the respective planes defined by each of the first side surface 18, the second side surface 20, the front surface 22, and the rear surface 24 of the body 16 at a plurality of different lengthwise, widthwise, and/or heightwise positions on the respective planes. In such embodiments, the orientation of the protrusions 32 can be randomly selected (e.g., by a drafting program or the like), or can have the appearance of being randomly selected.

Figure 15:
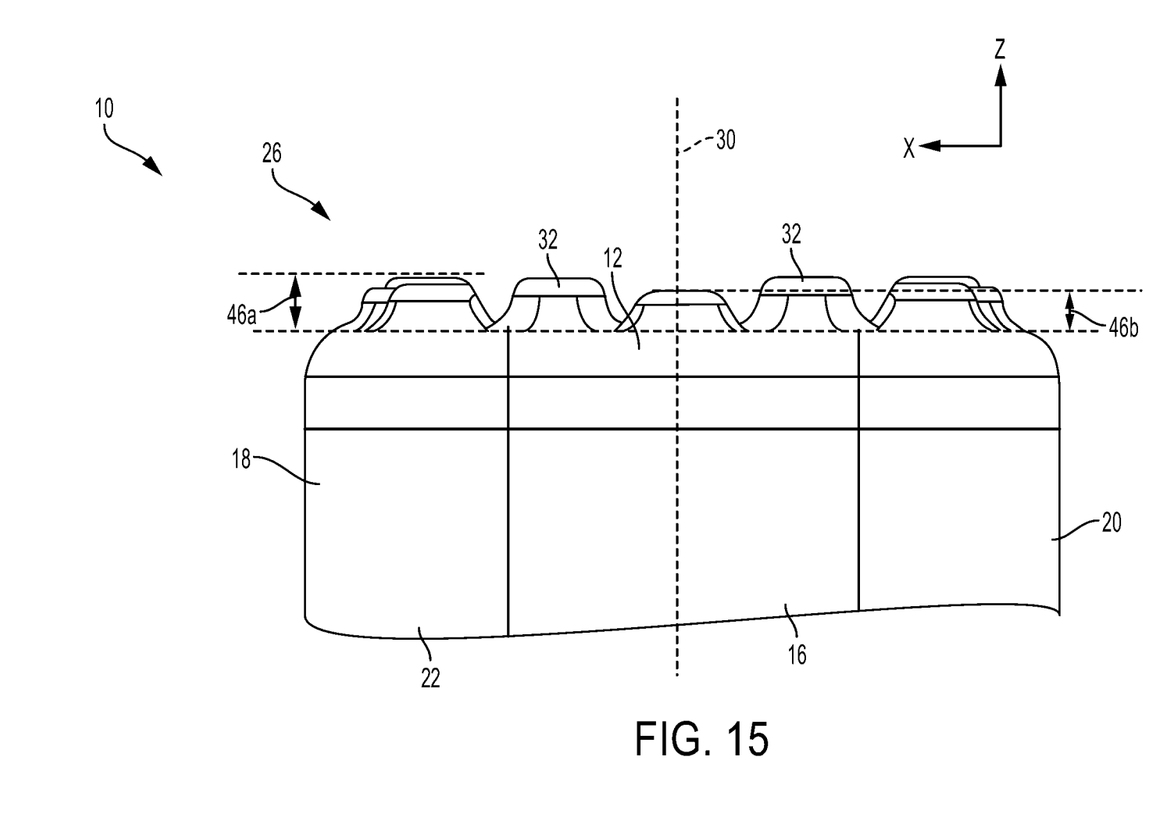
FIG. 15 illustrates a front elevation view of the top end portion of the spinal implant of FIG. 14.

Referring to FIGS. 8, 12, and 15, the protrusions 32 each define a height 46 equal to the distance extending between the respective bearing surface 12, 14 and the tip 36 of the respective protrusion 32 in a direction at least substantially parallel to the body axis 30. The heights 46 of the protrusions 32 can vary depending on the procedure for which the spinal implant 10 is to be used, one or more physiological facts of the patient (e.g., sizes of the patient's vertebrae), and/or one or more other design considerations. In some embodiments, for example, the heights 46 of the protrusions 32 are between 1 mm and 3 mm. In some embodiments (see FIGS. 8 and 12), the protrusions 32 all have substantially the same height 46. In other embodiments (see FIG. 15), the respective protrusions 32 of at least one of the first and second bearing surfaces 12, 14 have a plurality of different heights 46a, 46b. In such embodiments, the different heights 46 can be achieved by varying the height at which one or more of the protrusions 32 are truncated, blunted, and/or rounded. The different heights 46 can additionally or alternatively be achieved by providing the base 34 of one or more of the protrusions 32 with a different shape relative to the bases 34 of the other protrusions 32 on the respective bearing surface 12, 14, and/or by providing one or more protrusions 32 with a different angle 44 relative to the other protrusions 32 on the respective bearing surface 12, 14. In some embodiments, the protrusions 32 can have heights 46 that are randomly selected (or that have the appearance of being randomly selected) to be with a predetermine height range (e.g., 1 mm to 3 mm).

In some embodiments, including the illustrated embodiments, the body 16 of the spinal implant 10 includes an aperture 48 extending between the first and second bearing surfaces 12, 14.

In some embodiments, a known fixation device (not shown) can be used to prevent movement of the spinal implant 10 relative to one or more vertebrae.

The cost and logistics of manufacturing a spinal implant 10 having protrusions 32 as described above (e.g., with tips 36 that overhang the bases 34) makes conventional manufacturing techniques (e.g., subtractive manufacturing techniques, machining, etc.) impossible. Accordingly, a method for manufacturing the spinal implant 10 involves use of selective laser sintering (SLS), which is an additive manufacturing technique that uses electromagnetic radiation from a laser to fuse small particles of powders into a mass that has a desired three-dimensional shape.

The present method involves the following steps, the order of which can vary: (i) using a laser to selectively fuse powdered material by scanning two-dimensional cross-sections according to a three dimensional digital description of the part (also known as a "build file") on the surface of a powder bed; (ii) after a cross-section is scanned, lowering the powder bed by one layer thickness; (iii) applying a new layer of material; and (iv) rescanning the powder bed. Steps (i)-(iv) are repeated until the desired three-dimensional shape part is completed.

The powder bed used in the method includes a polymeric powder material, including, for example, a polyaryletherketone ("PAEK") powder material. PEAK powder materials are particularly useful here because they are characterized by a low flammability, a good biocompatibility, and a high resistance against hydrolysis and radiation. The thermal resistance at elevated temperatures as well as the chemical resistance distinguishes PAEK materials from ordinary plastic powders. A PAEK powder material can include be one or more powder materials selected from the group consisting of polyetheretherketone ("PEEK"), polyetherketone ketone ("PEKK"), polyetherketone ("PEK"), polyetheretherketoneketone ("PEEKK") or polyetherketoneetherketoneketone ("PEKEKK").

In some embodiments, it can be especially advantageous to use a PEKK powder material, available under the brand name OXPEKK® from Oxford Performance Materials, Inc. in South Windsor, Conn. Specimens fabricated from OXPEKK® polymer have been subjected to biocompatibility testing according to ISO 10993 and USP <85> standards, and have met all applicable criteria for devices with permanent bone and tissue body contact with the additional potential to contact the cerebrospinal fluid. Such test specimens have been subjected to a successful sterilization validation. It should be understood that there are different blends of PEKK powder materials. Unlike other PAEK materials, PEKK is a copolymer (AB type EKK/EKK). The examples described herein pertain to the 60/40 PEKK copolymer sold under brand name OXPEKK®. It should be understood, however, that the present invention is not limited to any specific blend of PEKK resin, and that different blends may be used.

In embodiments in which the method involves an unused PEKK powder material, the method can additionally or alternatively include one or more of the following steps, the order of which can vary: (a) verifying that that the unused PEKK powder material is adequately dry; (b) loading the unused PEKK powder material into a SLS machine; (c) loading the PEKK powder material is loaded into a hopper, or the like, from which an SLS machine can distribute sequential layers of powder onto a powder bed of the SLS machine for sintering; (d) loading the part geometries (also known as the "build definition") into a computer associated with the SLS machine; (e) pre-heating the SLS machine according to known methods; (f) setting the bed temperature to a temperature as determined by characterization of the PEKK powder material; (g) setting the laser power to a power specified by the vendor and/or to a power determined from earlier runs of the SLS process; (h) setting a powder layer thickness (e.g., 125 microns); (i) after the layer-wise build is performed, cooling the resulting powder cake at a controlled rate (e.g., between 1 and 100 degrees Celsius per hour); (j) after powder cake has achieve at least substantially room temperature, removing the spinal implant 10 therefrom. Regarding step (i), it should be appreciated by a person having ordinary skill in the art that the rate of cooling depends on the dimensions of the cake, with deeper beds typically requiring more time to cool.

While several embodiments have been disclosed, it will be apparent to those of ordinary skill in the art that aspects of the present invention include many more embodiments and implementations. Accordingly, aspects of the present invention are not to be restricted except in light of the attached claims and their equivalents. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

What is claimed is:

1. A medical implant, comprising:
a body extending between a first end portion and a second end portion thereof;
a first bearing surface disposed relative to the first end portion;
the first bearing surface defining a plurality of protrusions which each extend along a respective protrusion axis that passes through a respective apex of the respective protrusion;
wherein the respective protrusion axes extend in different random directions towards and/or away from a same body axis extending between the first end portion and the second end portion of the body;
wherein the plurality of protrusions comprise a first pair protrusions, a second pair of protrusions, and a third pair of protrusions;
wherein the each of the first pair of protrusions are adjacent to each other, each of the second pair of protrusions are adjacent to each other, and each of the third pair of protrusions are adjacent to each other;
wherein an angle β is formed between the first pair of protrusions, an angle α is formed between the second pair of protrusions, and an angle γ is formed between the third pair of protrusions;
wherein each of the angle β, α, γ are different.

2. The medical implant of claim 1 comprising polyaryletherketone (PAEK).

3. The medical implant of claim 2 comprising one or more of the following: polyetheretherketone ("PEEK"), polyetherketone ketone ("PEKK"), polyetherketone ("PEK"), polyetheretherketoneketone ("PEEKK") or polyetherketoneetherketoneketone ("PEKEKK").

4. The medical implant of claim 2, wherein a tip of one or more of the plurality of protrusions is truncated.

5. The medical implant of claim 2, wherein one or more of the plurality of protrusions form teeth extending from the first bearing surface.

6. The medical implant of claim 3, wherein the medical implant comprises PEEK.

7. The medical implant of claim 3, wherein the implant comprises PEKK.

8. The medical implant of claim 3, wherein the implant comprises PEKK.

9. The medical implant of claim 1, wherein the plurality of protrusions are configured to support fusion.

10. The medical implant of claim 1 comprising polyaryletherketone (PAEK).

11. The medical implant of claim 10 comprising one or more of the following: polyetheretherketone ("PEEK"), polyetherketone ketone ("PEKK"), polyetherketone ("PEK"), polyetheretherketoneketone ("PEEKK") or polyetherketoneetherketoneketone ("PEKEKK").

12. The medical implant of claim 11, wherein the medical implant comprises PEEK.

13. A medical implant, comprising:
a body extending between a first end portion and a second end portion thereof;
a first bearing surface disposed relative to the first end portion;
the first bearing surface defining a plurality of protrusions which each extend along a respective protrusion axis that passes through a respective apex of the respective protrusion, the plurality of protrusions comprising a first pair protrusions, a second pair of protrusions, and a third pair of protrusions;
wherein each of the first pair of protrusions are adjacent to each other, each of the second pair of protrusions are adjacent to each other, and each of the third pair of protrusions are adjacent to each other;
wherein various angles are formed between directly adjacent protrusion axes of the first pair of protrusions, the second pair of protrusions, and the third pair of protrusions.

14. The medical implant of claim 13, wherein an angle β is formed between the first pair of protrusions, an angle α is formed between the second pair of protrusions, and an angle γ is formed between the third pair of protrusions.

15. The medical implant of claim 14, wherein each of the angle β, α, γ are different.

16. The medical implant of claim 14, wherein the PAEK comprises a selectively laser sintered PAEK.

* * * * *